United States Patent
Collins et al.

(10) Patent No.: US 9,085,512 B2
(45) Date of Patent: Jul. 21, 2015

(54) MODULARIZED SYSTEM AND METHOD FOR UREA PRODUCTION USING STRANDED NATURAL GAS

(75) Inventors: Terry R. Collins, Stillwater, OK (US); James L. Simonton, Lubbock, TX (US); Mario G. Beruvides, Lubbock, TX (US); Jessie Lozada, Shallowater, TX (US)

(73) Assignee: 4A Technologies, LLC, Lubbock, TX (US)

( * ) Notice: Subject to any disclaimer, the term of this patent is extended or adjusted under 35 U.S.C. 154(b) by 307 days.

(21) Appl. No.: 13/389,239

(22) PCT Filed: Aug. 12, 2010

(86) PCT No.: PCT/US2010/045342
§ 371 (c)(1),
(2), (4) Date: Feb. 6, 2012

(87) PCT Pub. No.: WO2011/019928
PCT Pub. Date: Feb. 17, 2011

(65) Prior Publication Data
US 2012/0136172 A1    May 31, 2012

Related U.S. Application Data

(60) Provisional application No. 61/233,271, filed on Aug. 12, 2009.

(51) Int. Cl.
*C07C 273/00* (2006.01)
*C07C 273/04* (2006.01)

(52) U.S. Cl.
CPC .................................. *C07C 273/04* (2013.01)

(58) Field of Classification Search
CPC ...................................................... C07C 273/10
See application file for complete search history.

(56) References Cited

U.S. PATENT DOCUMENTS

| | | |
|---|---|---|
| 3,594,983 A | 7/1971 | Yearout |
| 6,448,441 B1 | 9/2002 | Wing-Chiu et al. |
| 2004/0013605 A1 | 1/2004 | Ramani et al. |
| 2008/0244975 A1 | 10/2008 | Johnston |

OTHER PUBLICATIONS

"Generation and Development of Processes and Technical Means for Extraction and Processing of the Offshore Field Well Production", Mastobaev Yu.B. Author's Summary, 2005 pp. 23-24.

*Primary Examiner* — Clinton Brooks
(74) *Attorney, Agent, or Firm* — GableGotwals

(57) ABSTRACT

A modular system and method for producing urea from stranded natural gas includes removal of foreign particulate matter to obtain a substantially homogeneous gas. The gas is processed by controlling the quality of the stranded natural gas to maintain a substantially homogenous mixture The resultant gas stream is further cleaned and compressed to a high pressure of about 3,000 psi. The resultant ammonia stream is processed in a bypass recycling loop system at 30% conversion rate at a high pressure of about 6,000 to 7,000 psi. The equipment associated with each of the process steps may be skid mounted for portability and/or contained within the footprint of a standard 48-foot flatbed trailer.

18 Claims, 7 Drawing Sheets

MODULARIZED SYSTEM AND METHOD FOR UREA PRODUCTION USING STRANDED NATURAL GAS

CROSS-REFERENCE TO PENDING APPLICATIONS

This application claims priority to, and the benefit of, U.S. Provisional Pat. App. No. 61/233,271, filed Aug. 12, 2009.

BACKGROUND OF THE INVENTION

The present invention relates generally to systems, methods and apparatuses for producing fertilizer and/or mixed fuels. More particularly, the invention relates to systems, methods and apparatuses that use stranded natural gas as a feedstock to produce high nitrogen fertilizers such as urea.

The market for high nitrogen fertilizers such as urea (which contains about 46% nitrogen) continues to grow. For example, U.S. domestic consumption of urea has experienced a 1.2% growth rate per year for the past six years. In 2008, North American consumption exceeded 6.5 million tons while domestic production was less than 4.5 million tons. Consequently, the balance had to be supplemented with imported product.

The growth in demand for urea stems from its versatility, portability, and capability. Urea has various uses, including use as an agricultural fertilizer, as raw material input for production of plastics, and use by the surfactant industry. Moreover, urea is compatible with the local and regional markets for the product. Further, urea is also beneficial due to manufacturing cost per ton of production. Additionally, urea has a number of advantages over other nitrogen fertilizers. For example, urea is safer to ship and handle and is less corrosive to equipment. It also has a higher analysis than any other dry nitrogen fertilizer. Furthermore, the high analysis means a reduced transportation and application cost per pound of nitrogen. It can also be applied in many different ways, from sophisticated aerial application equipment to manual hand spreading. Urea is also highly water soluble so it moves readily into the soil. In addition, it can be used on virtually all crops. Another benefit is that the manufacturing of urea releases few pollutants to the environment. Urea can also be stored and distributed through conventional systems.

The advantages of urea relative to other fertilizers helps make urea the major fertilizer traded in international commerce. In the very near future, urea is expected to account for more than 50% of the nitrogen fertilizer in world trade. When compared to other dry fertilizers, urea has captured more than 65% of the world fertilizer trade.

Currently, over 90% of the urea produced utilizes natural gas as the feedstock. Over the past several years, natural gas costs have risen dramatically. In some cases, a 50% increase has been realized. During the winter of 2000-01, natural gas prices experienced a 400% increase. Because of natural gas prices, U.S. domestic nitrogen fertilizer production has dropped and imports have risen.

Urea production is natural-gas intensive. To produce one ton of nitrogen fertilizer from natural gas requires the consumption of between 20,000 and 33,800 cubic feet of natural gas. Utilizing 33,800 cubic feet per ton as an example, and considering each cubic foot of natural gas contains 1031 BTU's; one ton of fertilizer made from natural gas contains the equivalent of over 34.8 million total BTU's. In terms of gasoline equivalents, this would amount to over 300 gallons of gasoline per ton of fertilizer produced. Therefore, producing urea from normal sources of natural gas (i.e., non-stranded sources) is a costly proposition.

The use of stranded or flared natural gas sources, which are economically unviable for oil producers, could become a viable source of feedstock for urea production only if the quality of the incoming gas stream could be controlled and a low cost small production facility could be made available which does not require the high BTU content of the typical natural gas stream. Current global natural gas reserves total approximately 6,100 trillion cubic feet (tcf), according to U.S. Energy Administration Information estimates. Of these, roughly half are considered to be "stranded," that is, uneconomical to deliver to market. In addition, the World Bank estimates that over 150 billion cubic meters (bcm) of stranded natural gas are flared annually. When dealing with stranded natural gas, oil producers often find the energy, or BTU content, is too low; the gas is too impure to use; or, the volume is too small to warrant a pipeline connection to the gas infrastructure. In addition, the stranded gas is sometimes produced along with the oil, becoming an environmental liability. This unwanted, non-commercial by-product of oil production has become a major problem in oil fields where producers have been forced to abandon well sites early, leaving valuable reserves of domestic oil untapped.

Typically, there are three ways to deal with stranded gas: (1) venting or flaring the gas, which contributes to air pollution without any beneficial offsets from the gas; (2) using electrical energy to re-inject the gas, which incurs significant extra costs; and (3) shutting down oil production, which leaves valuable oil in the ground.

Another form of stranded natural gas is "associated gas," or gas found in association with development of large oil fields. While crude oil can be transported to distant markets with relative ease, the practice in the past has been to flare associated gas at the wellhead. This practice however is no longer acceptable due to environmental concerns and, more recently, due to the growing economic value of these reserves in a high-energy price environment. Oil producers are now looking to use technology to capture associated gas (stranded gas) and take it to consuming markets.

SUMMARY OF THE INVENTION

A modularized method for producing a fertilizer or a fuel from a stranded natural gas feedstock includes the steps of:
  i. capturing a natural gas feedstock that includes at least one stranded natural gas feedstock from at least one stranded natural gas source;
  ii. removing moisture from the captured natural gas feedstock;
  iii. removing potential disruptive inorganics and organics from the substantially moisture-free natural gas feedstock;
  iv. reformulating the substantially clean natural gas feedstock;
  v. recovering a carbon dioxide ($CO_2$) stream from the reformulated natural gas feedstock; and
  vi. combining the recovered $CO_2$ stream with an ammonia ($NH_3$) stream to form at least one of a fertilizer and a fuel.

Although the method is designed primarily for low volume production, the equipment embodying the method may be placed in series or in parallel with other sets of equipment embodying the method in order to increase production volumes.

To make efficient, economical use of the stranded gas and achieve fertilizer or fuel yields per volume of feedstock comparable to that of much larger, conventional plants which rely upon higher quality natural gas, quality control is especially important. For example, unlike a conventional plant that has a relatively consistent quality of gas feedstock, the stranded or flared gas streams that are used in this method vary in their processing characteristics, pressures, and volumes. Rather than adjusting process parameters to accommodate the incoming feedstock, the incoming feedstock is blended to form a substantially homogenous blend (albeit a still lower quality than that of the natural gas feedstock to a conventional plant). The homogenous blend may have, for example, a consistent BTU value or sulfur content. Similarly, the moisture removal step removes moisture to a predetermined moisture content, regardless of the source of the incoming feedstock. Further, processing temperatures and pressures are maintained within a desired range rather than changing in response to feedstock quality. A portion of the reformulating step, therefore, occurs in a temperature range of about 500° to 800° C. and the resultant $CO_2$ stream is compressed to a pressure of about 3,000 psi.

Unlike the prior art systems, the method includes a bypass loop recycle system at 30% conversion rate run at very high pressures (about 6,000 to 7,000 psi) which results in almost 100% conversion rates. The higher pressures allow for better separation of the chemical break-down during the creation of the ammonia. This conversion performance cannot be achieved with the same level of productivity by the high volume, low pressure processes in common use in today's industry. These prior art processes run at pressures approximately one-half the pressure of the process described herein.

The processing of stranded and flared natural gas using this method can also be used with modifications to generate other usable products. Unlike the prior art methods, which seek to optimize each and every step of the process, the method according to this invention incorporates the concept of systems "sub-optimization" developed by the American scholar and researcher Dr. W. Edwards Deming. The concept of sub-optimization states that a whole process (system) may result in sub-optimized performance by optimizing each individual sub-process (sub-system). True systems optimization is obtained by sub-optimizing the performance of the sub-system, when necessary, to achieve the optimization of the whole or complete system. Requiring additional in-process equipment, capital expenditure and processing time optimizes the critical processes of ammonia/urea production, and thereby makes feasible the processing of stranded natural gas to usable and viable products.

A urea production plant made according to this process preferably incorporates a modular construction, another unique feature of the invention. The plant is based on a five module configuration that is designed to minimize on-sight erection and start-up time/cost. The total package design improves the overall reliability along with flexibility. Preferably, all of the equipment associated with each of the modules is temporarily mounted within a footprint of a standard flatbed truck trailer. This temporary mounting may occur on the truck trailer itself or on a concrete pad about the size of the truck trailer. Regardless of whether the equipment is mounted on a truck trailer (or skid-mounted) and moved, or disassembled from the pad and then moved, the plant is easily and readily transported from one site to the next.

Modular construction minimizes the footprint of the production units while maintaining ease of operation and maintenance. Modular construction increases the ease with which updates and modifications can be performed as well as allowing units to be built in a central location and shipped anywhere around the world, or manufactured in the country of operation using standardized plans and specifications. In addition, modularization allows for the upgrade of the production plant by replacing specific modules when technical advances in such modules are developed without affecting the other modules that comprise the whole system (plant). This also allows for reduced downtime for process upgrades and maintenance.

DETAILED DESCRIPTION OF THE PREFERRED EMBODIMENTS

Figure 1:
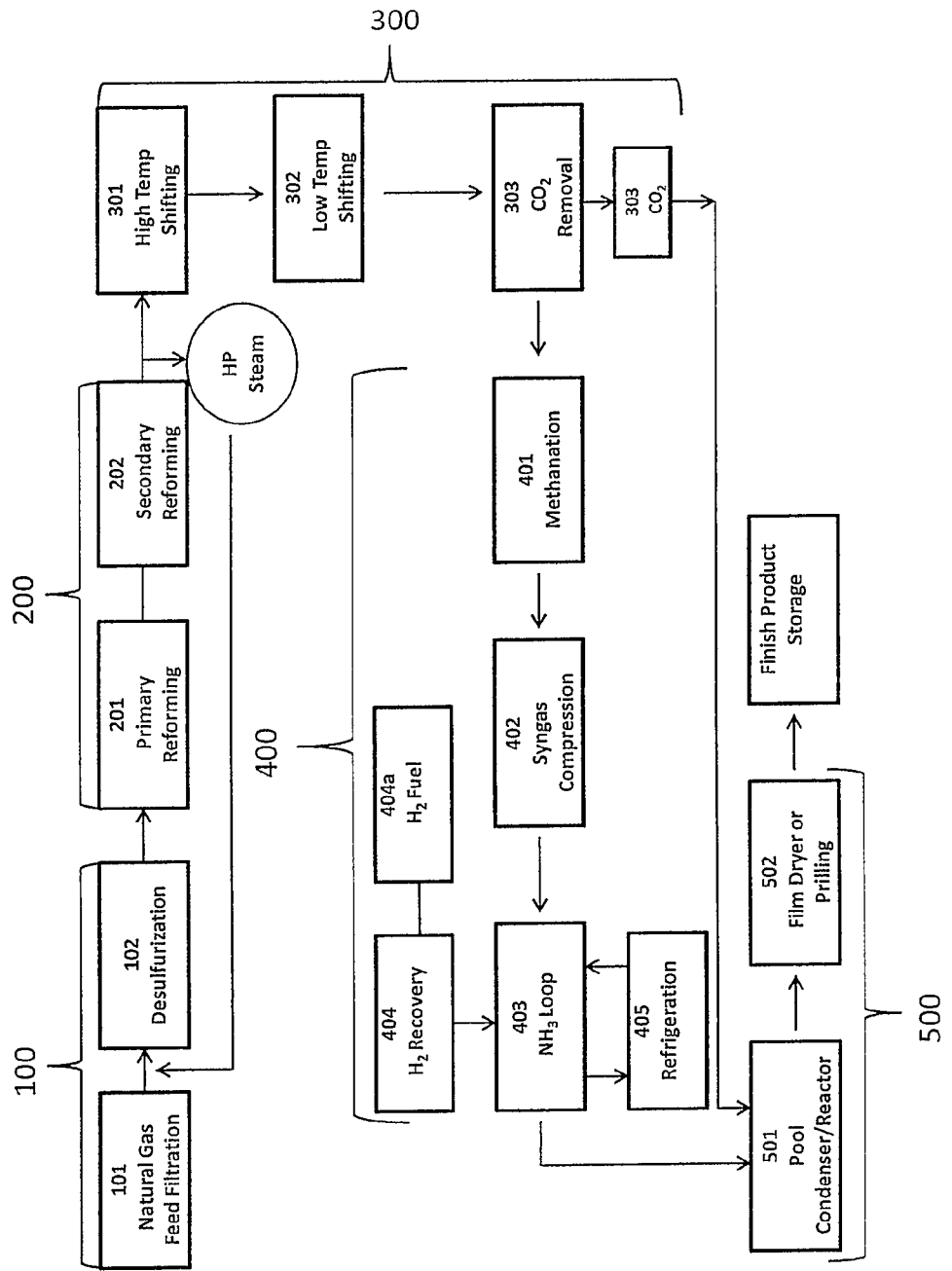
FIG. 1 is a process flow diagram of a urea production process that converts Stranded/Flared Natural Gas into urea. The gas is cleaned prior to being fed into a gasification unit.

The following disclosure provides many different embodiments, or examples, for implementing different features of the invention. These are, of course, merely examples and are not intended to limit the invention from that described in the claims. Well known elements are presented without detailed description in order not to obscure the present invention in unnecessary detail. For the most part, details unnecessary to obtain a complete understanding of the present invention have been omitted inasmuch as such details are within the skills of persons of ordinary skill in the relevant art.

Current plants for the production of high nitrogen fertilizers are large-scale, permanent facilities that take several years to build. To be economically viable, these plants, and their associated processing methods and equipment, require commercial grade natural gas at sufficient volume and pressure. Because the sources of stranded natural gas are geographically scattered, the quality of the gas is poor, and the volumes and pressures of the gas produced are relatively low, the gas is not a viable feedstock for these plants.

Unlike conventional plants, a production plant made according to the present invention can be built in about half the time. Because the cost of the plant is relatively low, and because the plant makes use of different ways to treat the gas feedstock, the plant is economically viable to produce high nitrogen fertilizers such as urea and other mixed fuels. Further, because the plant is modularized, the plant may be sited on a mobile pad (such as a flatbed trailer) or temporally sited on a concrete pad and then deconstructed, moved, and reconstructed in a matter of a few months. The modularized design of the plant allows the plant to go to the sources of stranded natural gas rather than require those sources come to it. This makes the design ideal for use in remote rural areas that have geographically scattered or low producing well sites, or areas that produce low quality gas or lack the infrastructure necessary to move large quantities of gas over long distances to a central location. Last, because of the design's modularity, the plants are easily maintained, self-sufficient and highly automated. This lends itself well to operating in remote well head locations.

The use of stranded natural gas for the production of urea is based on utilizing approximately 30,000 cubic feet of stranded natural gas having an average BTU content of 1,000 BTU per cubic foot to produce one ton of nitrogen fertilizer. Based on this relationship, the following production estimates are derived:

| Stranded Gas Feedstock in CF/hr (000) | Yield Urea (ton/hr or TPH) |
|---|---|
| 40.5 | 1.35 |
| 82.5 | 2.75 |
| 124.8 | 4.16 |

Achieving yields using stranded gas feedstock that are comparable to those using higher quality natural gas is a result of the unique and inventive characteristics of the method disclosed and claimed herein. Preferably, embodiments of the present invention are available in 1.35, 2.75 and 4.16 TPH sizes.

Regardless of TPH size, a plant made according to this invention may be paralleled or placed in series with other like-made plants to produce electrical power or bio-liquids (e.g., gasoline, diesel, jet fuel, fertilizers and other chemicals) in larger quantities. When compared to conventional plants, the smaller TPH size, provides many advantages, including: improved reliability; customizability; efficiency; portability; economy; compact units; environmentally friendly (meeting, for example, Environmental Protection Agency regulations and Texas Commission on Environmental Quality regulations) and operational ease.

The modular construction of the present invention also allows a user to optimize production based on the availability of stranded natural gas in a particular field. The modular construction also allows for the movement of the plant when a field or well becomes nonproductive.

I. Urea Production

Purification Module 100

The system and process of the present invention will now be described in the following paragraphs referring to FIG. 1.

The purification module 100 starts with filtering step 101 to reduce the moisture content of the stranded natural gas stream and obtain a substantially water-free fuel mixture of nitrogen and hydrogen in the stoichiometric ratio of 1:3. Once the moisture content is reduced to a predetermined level, high pressure steam is introduced to heat the fuel mixture to approximately 400° C. The heated fuel mixture is passed over a catalyst to remove potential disruptive inorganics and organics from the mixture. The catalyst converts nonreactive organic sulfur compounds to hydrogen sulfide. Hydrogen sulfide is removed by passing the mixture over a bed of zinc oxide particles in the desulfurizing step 102. The zinc oxide particles absorb the hydrogen sulfide. The purified gas stream is then ready for the reforming module 200.

Filtering step 101 or desulfurizing step 102 may be proceeded by a blending step (not shown) in which two or more different stranded natural gas streams are blended together to form a single substantially homogeneous stream. The importance of creating a homogenous feedstock when using biomass to produce urea is discussed in our earlier international application PCT/US2009.053537, titled "Modularized System and Method for Urea Production Using a Biomass Feedstock," published as WO/2010/019662 on Feb. 18, 2010, the content of which is hereby incorporated by reference.

Blending the streams to produce a single stream is important when using stranded natural gas because the gas produced by different well sites may have different processing characteristics, such as the amount of moisture, sulfur or BTU content. Failing to provide downstream modules with a consistent quality of gas (regardless of whether that quality is relatively high or low) makes it difficult to control the processes associated with those downstream modules and produce an end product having consistent quality. "Consistent quality" means in a state of statistical control. Unlike prior art processes, which require a certain quality of natural gas, the process described herein makes use of whatever quality of gas is available. For this reason, stranded natural gas is acceptable as a feedstock and could, if desired, be blended together with a higher quality, commercial-grade natural gas stream and processed.

Reforming Module 200

The reforming module 200 starts with a primary reforming step 201 in which the purified gas stream from Module 100 flows into indirectly heated tubes filled with nickel containing a reforming catalyst. The indirectly heated tubes raise the temperature of the gas stream to about 500 to 800° C. In primary reforming step 201 the reaction is controlled to achieve only a partial conversion of approximately 65% based on the methane feed from module 100. In a subsequent secondary reforming step 202 the partially converted gas stream is passed through a refractory lined reaction vessel with nickel catalyst and mixed with a controlled amount of combustion air. The combustion of the partially converted gas stream further raises the temperature to approximately 1,200° C. The combusted gas stream then flows through another catalyst layer where the outlet temperature is lowered to approximately 1,000° C. and the residual methane is less than 0.5%. The outgoing reformed gas stream, which is compressed to at least 206 bar (about 3,000 psi), is then ready for shift conversion.

Shift Conversion Module 300

Shift conversion module 300 uses a water-gas shift reaction. The carbon monoxide (CO) serves as a reducing agent for water to yield hydrogen (H) and carbon dioxide ($CO_2$). Module 300 not only produces more H for ammonia module 400 but also converts the CO to $CO_2$ which will be used as a chemical component in the urea production module 500.

Shift conversion module 300 begins with step 301, high temperature shift conversion, which utilizes an iron-based catalyst with an additional 5 to 10% chromic oxide. Steam is introduced to the incoming reformed gas stream and the temperature of the reaction is held to a range of about 300 to 500° C. This is a controlled process and is dependent on the ratio of $CO/CO_2$.

Low temperature shift conversion step 302 utilizes an iron-chromium and copper-zinc catalyst that is active at a temperature range of about 320 to 360° C. Step 302 furthers the reaction and also works to absorb residual sulfur (<0.1 ppm) to prevent poisoning of the catalyst. $CO_2$ is stripped 303, 303a, compressed at approximately 206 bar (about 3,000 psi) and flowed to the urea conversion module 500.

Ammonia Module 400

Ammonia module 400 involves a purification process using a simple reversal of the primary reforming step 201 to reduce carbon oxides to less than 10 ppm. A nickel catalyst, at a pressure of about 25 to 35 bar (about 360 to 510 psi), controlled at temperature between about 250 to 350° C. is utilized in the methanation process step 401. The processed gas exiting step 401 is then compressed in syngas compression step 402 at approximately 150 to 175 bar (about 2,175 to 2,550 psi) and flowed to the ammonia convertor loop 403. The ammonia convertor loop 403 is used to continuously recycle the gas over an iron catalyst using a $H_2$ recovery feed 404, 404a. A refrigeration loop 405 is utilized to cool the gas after passing over the catalyst which allows for the pure ammonia ($NH_3$) to condense out. Ammonia converter loop 403 is a bypass recycling loop at a high pressure range of between about 410 to 485 bar (about 6,000 to 7,000 psi) and results in about a 30% conversion rate.

Urea Conversion Module 500

Figure 4:
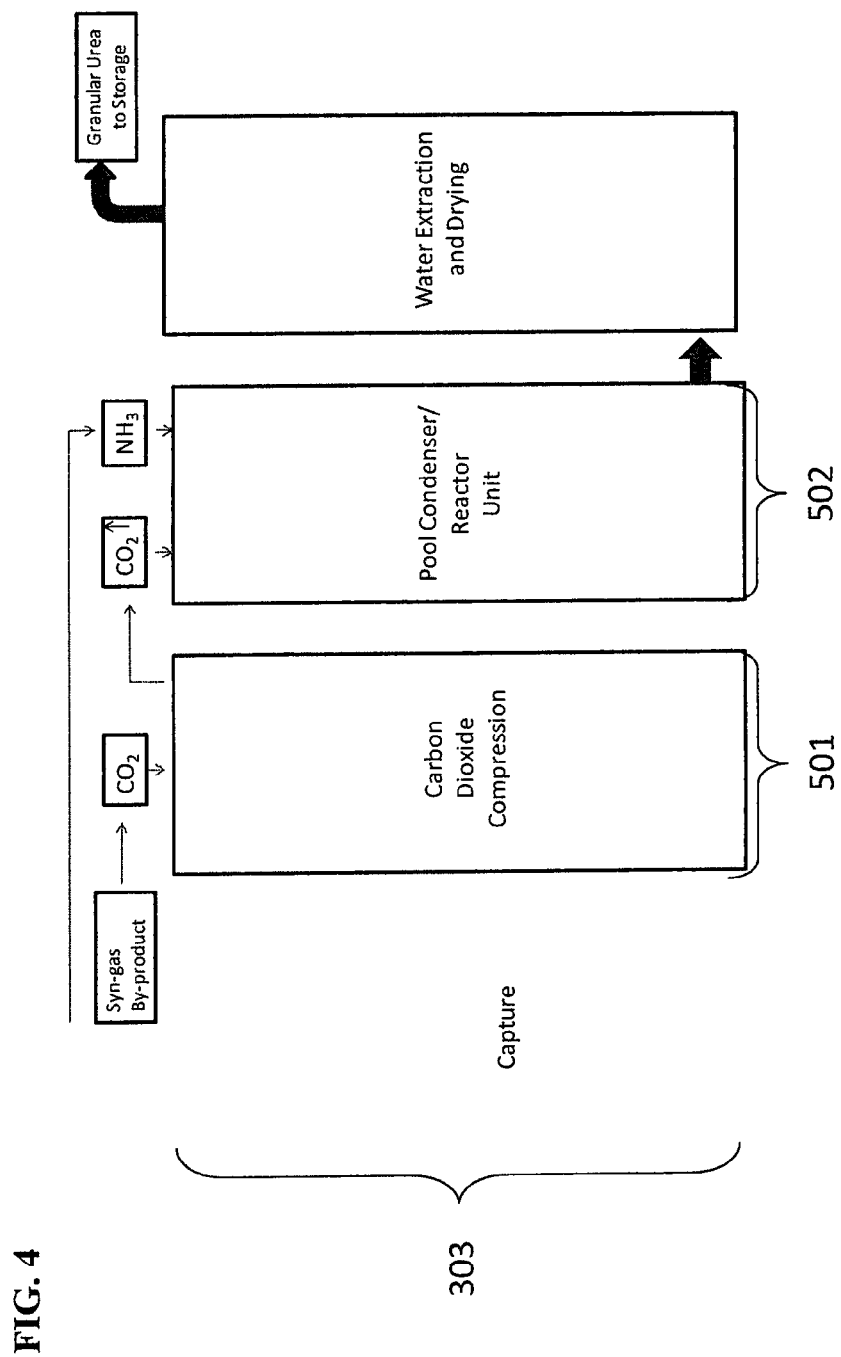
FIG. 4 is a schematic representation of the interrelationship between the carbon dioxide compression component, condenser/reactor, and water extraction and drying components of the urea conversion module and the gas stream.
Figure 5:
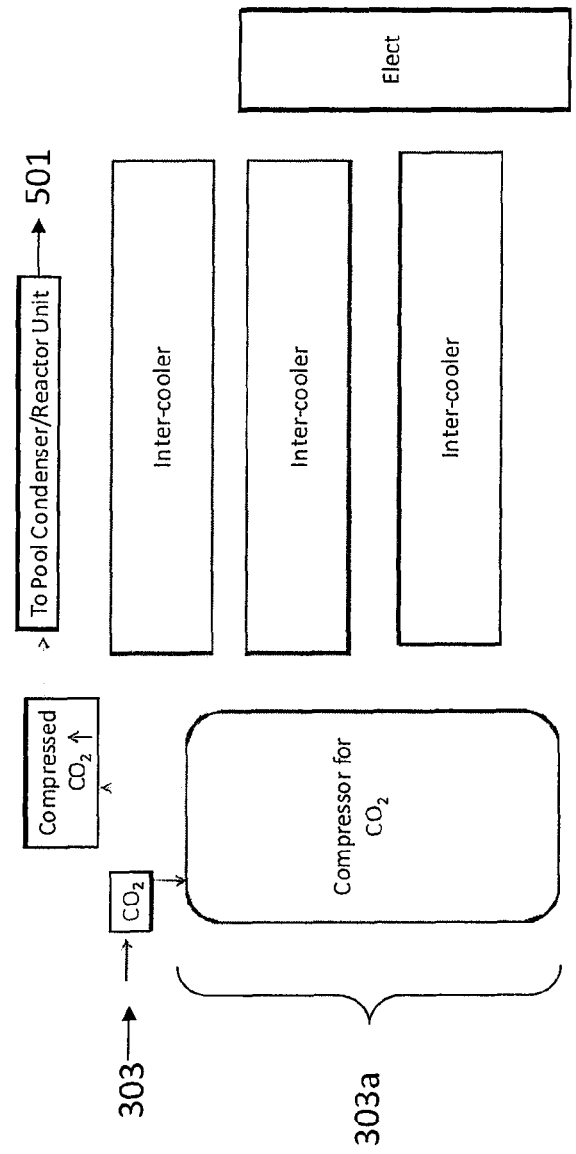
FIG. 5 is a schematic representation of the carbon dioxide compression component of the urea conversion module.

Urea production module 500 is described in our previously mentioned international application. Urea conversion module 500 receives the compressed $CO_2$ from step 303a and the $NH_3$ from step 403 and flows the compressed $CO_2$ and $NH_3$ to a pool condenser step 501 (see FIGS. 4, 5 & 6). $NH_3$ and $CO_2$ are introduced into the pool condenser 501a by a high-pressure ammonia pump and a carbon dioxide compressor (see FIG. 6). The $CO_2$ and $NH_3$ gas streams are flowed countercurrent to one another in order to improve the overall reaction within the pool condenser 501a. About two-thirds of the urea conversion takes place in the pool condenser 501a. After the pool condenser 501a the remaining gases and urea-carbamate liquid enter the vertical pool reactor 501b in which the final urea formation takes place. Any un-reacted carbamate may be routed to a scrubber/recycler 501c for reintroduction to vertical pool reactor 501b.

Figure 7:
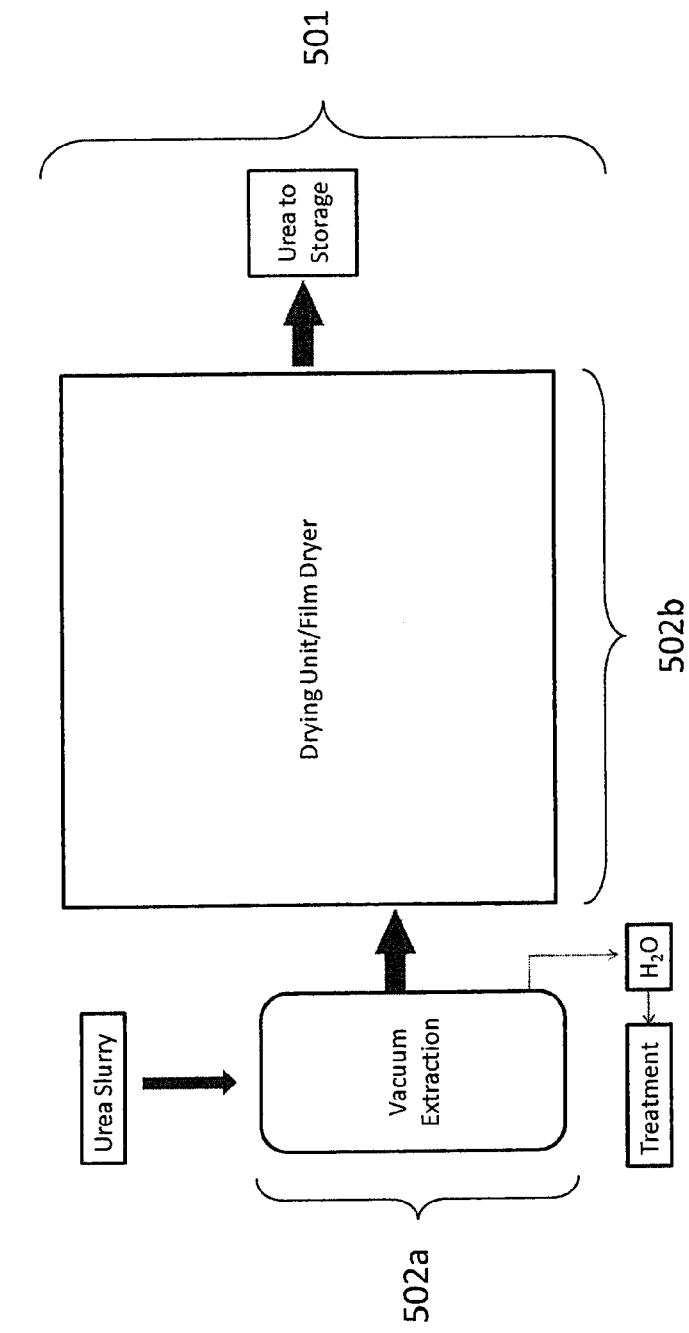
FIG. 7 is a schematic representation of the water extraction and drying component of the urea conversion module.

The resulting urea slurry or solution is sent to a drying step 502 where water is removed (see FIG. 7). Water extraction occurs by way of vacuum extraction 502a. The remaining urea melt is then sent to a drying unit or film dryer (granulation) 502b where it is further dried using a film drying process to result in a final product to be stored. The water removed from vacuum extraction 502a, and from film dryer 502b, is preferably recycled through the system but may be treated and discharged.

II. Modular Arrangement

Figure 2:
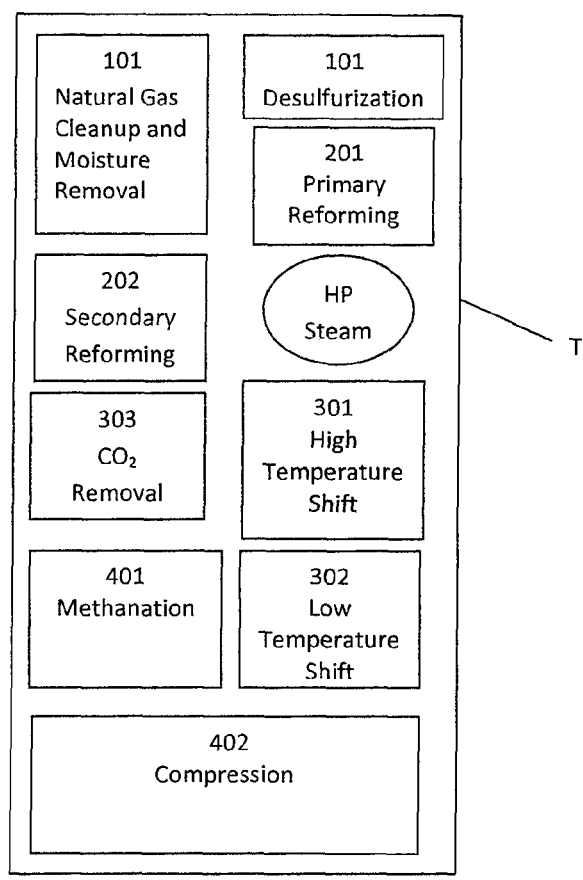
FIG. 2 is a block layout of the gasification system module arranged on a standard 48-foot flatbed trailer.
Figure 3:
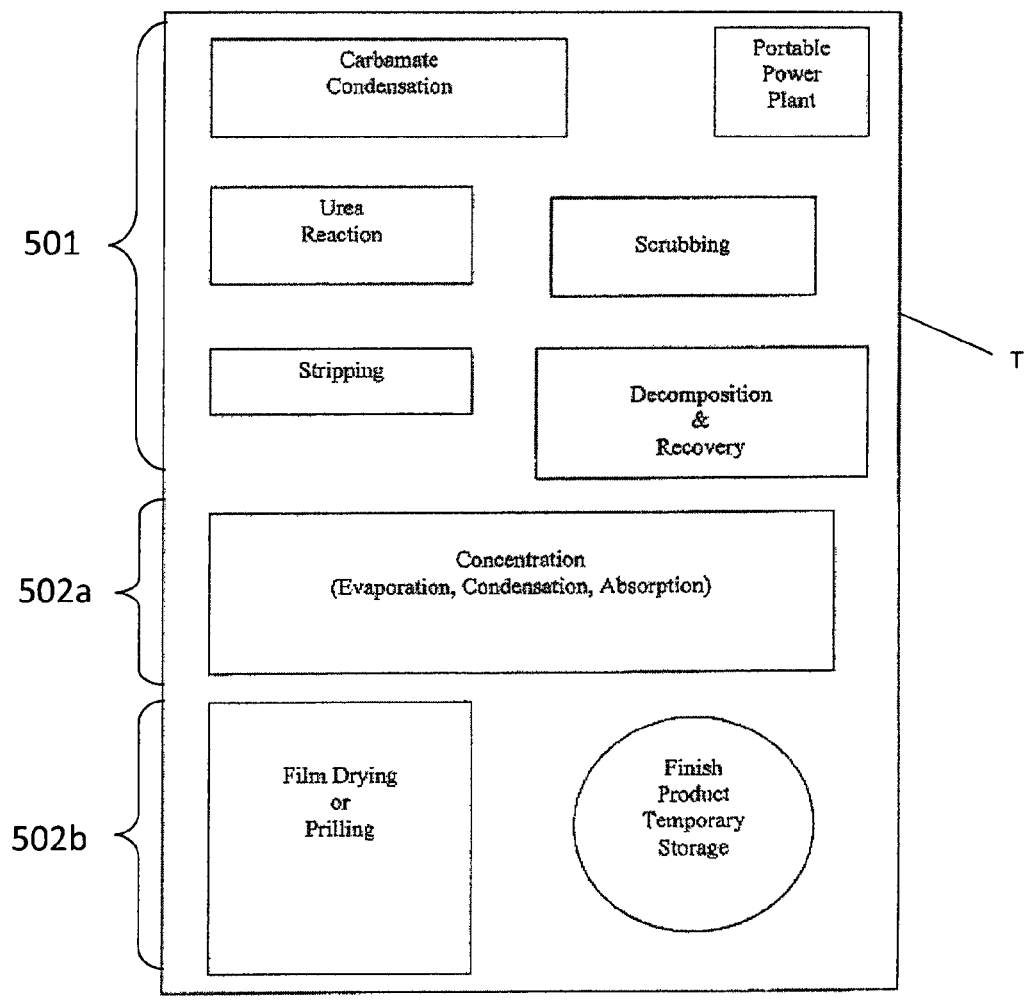
FIG. 3 is a block layout of the urea conversion module arranged on a standard 48-foot flatbed trailer.

Referring now to FIGS. 2 and 3 (and referring back to FIG. 1), the urea production process may be a modularized process, with process steps 101 to 102 comprising purification module 100, steps 201 to 202 comprising reforming module 200, steps 301 to 303 comprising shift conversion module 300, steps 401 to 405 comprising the ammonia module 400, and steps 501 to 502 comprising a urea conversion module 500. In FIGS. 2 and 3, the various pieces of process equipment associated with each module have been mapped to the corresponding process steps of FIG. 1.

The purification module 100, reforming module 200, shift conversion module 300, ammonia module 400, and urea conversion module 500 may be arranged for turn-key operation preferably on a concrete pad (if a semi-permanent installation is required) or on standard 48-foot flatbed trailers T, respectively. If a smaller size flatbed trailer is used, it may be necessary to divide the individual component parts of the module 100, 200, 300, 400, or 500 into two or more flatbed trailers with appropriate connections being provided.

Each module 100, 200, 300, 400, and 500 is preferably skid-mounted for ease of offloading to a remote site. A portable power plant P may be provided to power one or more of the modules 100, 200, 300, 400, 500. Although the process flow and interconnections between various components are not shown in FIGS. 2 and 3 (as well as in FIGS. 4 to 7), a person of ordinary skill in the art would recognize the flow pattern and the types of connections required for various process components.

Figure 6:
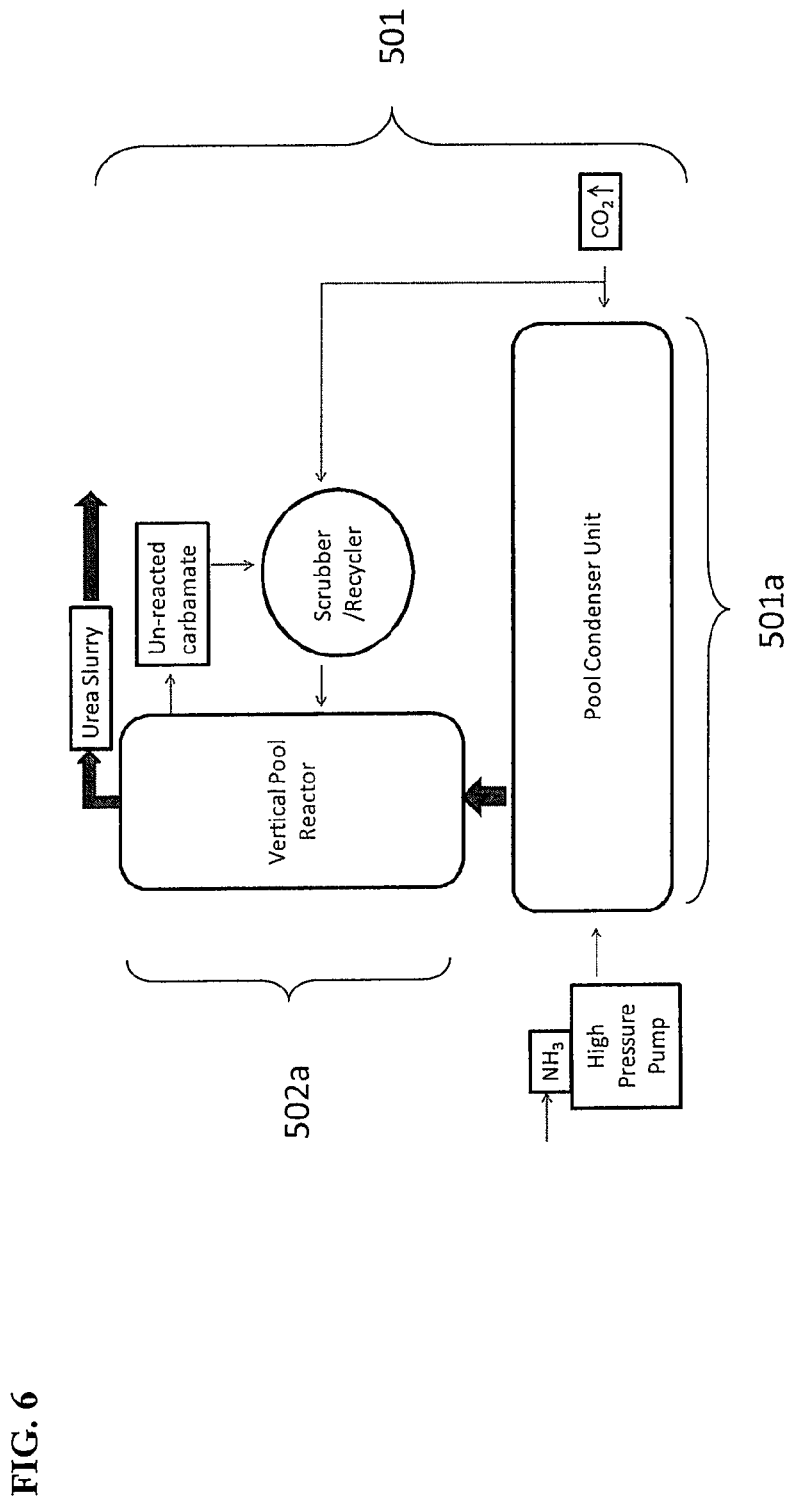
FIG. 6 is a schematic representation of the pool condenser/reactor component of the urea conversion module.

Referring now to FIGS. 6 to 7, an alternate preferred embodiment of urea conversion module 500 is shown which may be arranged so as to fit within the footprint of a standard 48-foot flatbed trailer T (or concrete pad). Similar to FIGS. 2 to 5 above, the various pieces of equipment associated with the urea conversion module 500 have been mapped to the corresponding process steps of FIG. 1.

While a modular system and method for urea production has been described with a certain degree of particularity, many changes may be made in the details of construction and the arrangement of components and steps without departing from the spirit and scope of this disclosure. A system and method according to this disclosure, therefore, is limited only by the scope of the attached claims, including the full range of equivalency to which each element thereof is entitled.

What is claimed is:

1. A method for producing urea from a stranded natural gas feedstock, the method comprising the steps of:
 i. capturing at a stranded natural gas source site a natural gas feedstock that includes at least two stranded natural gas feedstocks each coming from a different stranded natural gas source;
 ii. blending at the stranded natural gas source site the at least two captured stranded natural gas feedstocks with one another to form a blended natural gas feedstock having a BTU content less variable than a BTU content of the at least two captured stranded natural gas feedstocks;
 iii. removing moisture and potential disruptive inorganics and organics from the blended natural gas feedstock;
 iv. reformulating the clean blended natural gas feedstock;
 v. recovering a CO2 stream from the reformulated natural gas feedstock; and
 vi. combining the recovered CO2 stream with a NH3 stream to form the urea.

2. A method according to claim 1 wherein the at least two stranded natural gas feedstocks each have at least one different processing characteristic than the other.

3. A method according to claim 1 wherein the moisture removal step removes moisture to a predetermined moisture content.

4. A method according to claim 1 further comprising a portion of the reformulating step occurring in a temperature range of about 500° to 800° C.

5. A method according to claim 1 further comprising the reformulating step including the sub-step of compressing the resultant $CO_2$ stream to a pressure of at least about 3,000 psi.

6. A method according to claim 1 further comprising the step of processing the $NH_3$ stream in a bypass recycling loop.

7. A method according to claim 6 wherein the bypass recycling loop operates at a high pressure range of between about 6,000 to 7,000 psi and results in about a 30% conversion rate.

8. A method according to claim 1 wherein equipment embodying the method is placed in series with at least one other set of equipment embodying the method.

9. A method according to claim 1 wherein equipment embodying the method is placed in parallel with at least one other set of equipment embodying the method.

10. A method according to claim 1 wherein all equipment associated with at least one of the steps (i) to (vi) is portable between a first and second stranded natural gas source site.

11. A method according to claim 10 wherein all equipment associated with at least one of steps (i) to (vi) is temporarily mounted within a footprint of a standard flatbed truck trailer.

12. A method according to claim 10 wherein all equipment associated with at least one of the steps (i) to (vi) is skid mounted.

13. A method according to claim 1 wherein all equipment associated with at least one of the steps (i) to (vi) is temporarily positioned at a location in fluid communication with the at least two stranded natural gas source.

14. A system for producing urea from a stranded natural gas source, the system comprising:
    a purification module;
    a reformulation module;
    a shift conversion module;
    an ammonia module; and
    a urea conversion module;
    at least one of the modules being portable between a first and second stranded natural gas source site;
    wherein at least two stranded natural gas feedstocks are blended together, each of the at least two stranded natural gas feedstocks being from a different stranded natural gas source, the blended together stranded natural gas feedstock having a less variable BTU content than a BTU content of the at least two stranded natural gas feedstocks prior to being blended together.

15. A system according to claim 14 wherein the purification module provides the less variable BTU content.

16. A system according to claim 14 wherein a resultant gas stream from the reformulation module is compressed to a pressure of at least about 3,000 psi.

17. A system according to claim 14 wherein the ammonia module further comprises a bypass recycling loop operating in a high pressure range of between about 6,000 to 7,000 psi and resulting in about a 30% conversion rate.

18. A system for producing urea from a stranded natural gas source, the system comprising:
    a set of portable modules arranged in series, the set including at least one module each for purification, reformulation, shift conversion, ammonia, and urea conversion;
    the purification module including means for blending together stranded natural gas streams from different sources, the blended together stranded natural gas streams having a less variable BTU content than that of the stranded natural gas streams.

* * * * *